US00PP09327P

United States Patent [19]

Zary

[11] Patent Number: Plant 9,327

[45] Date of Patent: Oct. 17, 1995

[54] HYBRID TEA ROSE PLANT NAMED 'JACNUEL'

[75] Inventor: Keith W. Zary, Thousand Oaks, Calif.

[73] Assignee: Bear Creek Gardens, Inc., Medford, Oreg.

[21] Appl. No.: 316,913

[22] Filed: Oct. 3, 1994

[51] Int. Cl.[6] ..... A01H 5/00

[52] U.S. Cl. ..... Plt./11

[58] Field of Search ..... Plt./11, 18

*Primary Examiner*—Howard J. Locker

*Attorney, Agent, or Firm*—Klarquist Sparkman Campbell Leigh & Whinston

[57] ABSTRACT

A hybrid tea rose plant having vigorous, upright growth habit, very few thorns, novel flower color, resistance to powdery mildew, moderate fragrance, and good cut-flower production.

1 Drawing Sheet

The present invention relates to a new and distinct variety of rose plant of the hybrid tea class which was originated by me by crossing the variety JACsil, U.S. Plant Pat. No. 6,010, with the variety AROpoiz, U.S. Plant Pat. No. 6,812.

The primary objective of this breeding was to produce a new rose variety having the high production and lack of thorns of the female, combined with the large flower size, fragrance and long strong stems of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright growth habit;
2. Very few thorns;
3. Novel flower color;
4. Resistance to powdery mildew;
5. Moderate fragrance; and
6. Good cut flower production.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—JACsil.

*Pollen parent.*—AROpoiz.

Classification:

*Botanical.*—Rosa hybrida.

*Commerical.*—Hybrid tea.

FLOWER

Observations made from specimens grown in a greenhouse environment at Somis, Calif., from January to July 1994.

Blooming habit: Continuous.

Bud:

*Size.*—1½ inches long when the petals start to unfurl.

*Form.*—The bud form is long, pointed ovoid.

*Color.*—When sepals first divide, bud color is Greyed Purple 186C. When half blown, the upper sides of the petals are Greyed Purple 186C; and the lower sides of the petals are Greyed Purple 186C.

*Sepals.*—Color: Green Group 138C. Surface texture: Covered in fine hairs. There are three lightly appendaged sepals. There are two unappendaged sepals with hairy edges.

*Receptacle.*—Color: Green Group 143C. Shape: Funnel. Size: Large (⅝ inch×⅜ inch). Surface: Smooth.

*Peduncle.*—Length: Long (4 inches to 4½ inches). Surface: Smooth with an occasional small gland. Color: Medium green. Strength: Stiff, erect.

Bloom:

*Size.*—Large. Average open size is 5 inches.

*Borne.*—Singly.

*Stems.*—Long, strong. Average length is about 22 inches to 28 inches.

*Form.*—When first open: High centered. Permanence: Flattens, outer petals curl back.

*Petalage.*—Number of petals under normal conditions: 30.

*Color.*—The upper side of the petals is Greyed Purple 186C. The reverse side of the petals is Greyed Purple 186 C. The base of each petal has a small yellow half moon at the point of attachment (¼ inch×¼ inch). The major color on the upper side is Greyed Purple 186C.

*Variegations.*—Occasional green streak on the guard petals.

*Discoloration.*—The general tonality at the end of the first day: No change. At the end of the third day: No change. By the fifth day, when the flower is fully open while on the plant, there is a general fading of color to Greyed Purple 186D.

*Fragrance.*—Moderate.

Petals:

*Texture.*—Thick.

*Shape.*—Deltoid.

*Form.*—Tips slightly recurved, edges slightly quilled.

Arrangement.—Imbricated, with a few petaloids in the center.

*Persistence.*—Drop off cleanly.

*Lastingness.*—On the plant: Fair (6 to 7 days). As a cut flower: Fair (8 to 9 days).

Reproductive parts:

*Anthers.*—Size: Medium. Quantity: Many. Color: Yellow. Arrangement: Regular around styles, mixed with petaloids.

*Filaments.*—Color: Reddish.

*Pollen.*—Color. Lemon yellow.

*Styles.*—Color: Reddish.

*Stigmas.*—Color: Greenish white.

Form: Bush.

Growth: Very vigorous, upright, branching. At one year, in the greenhouse, the plant is 7 feet tall by 4 feet wide.

Foliage: Number of leaflets on normal mid-stem leaves: 5 or often 7.

*Size.*—Large (6 inches×4 inches).

*Quantity.*—Abundant.

*Color.*—New foliage: Greyed Red 178B. Old foliage: Green Group 139A on the upper side, and Green Group 138B on the lower side.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth with occasional small prickles.

*Stipules.*—Medium (½ inch), serrated.

*Disease resistance.*—Resistant to mildew under normal greenhouse growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Few. On laterals from main canes: Few.

*Form.*—Medium (¼ inch to 5/16 inch), hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its vigorous, upright growth habit, very few thorns, novel flower color, resistance to powdery mildew, moderate fragrance, and good cut-flower production.

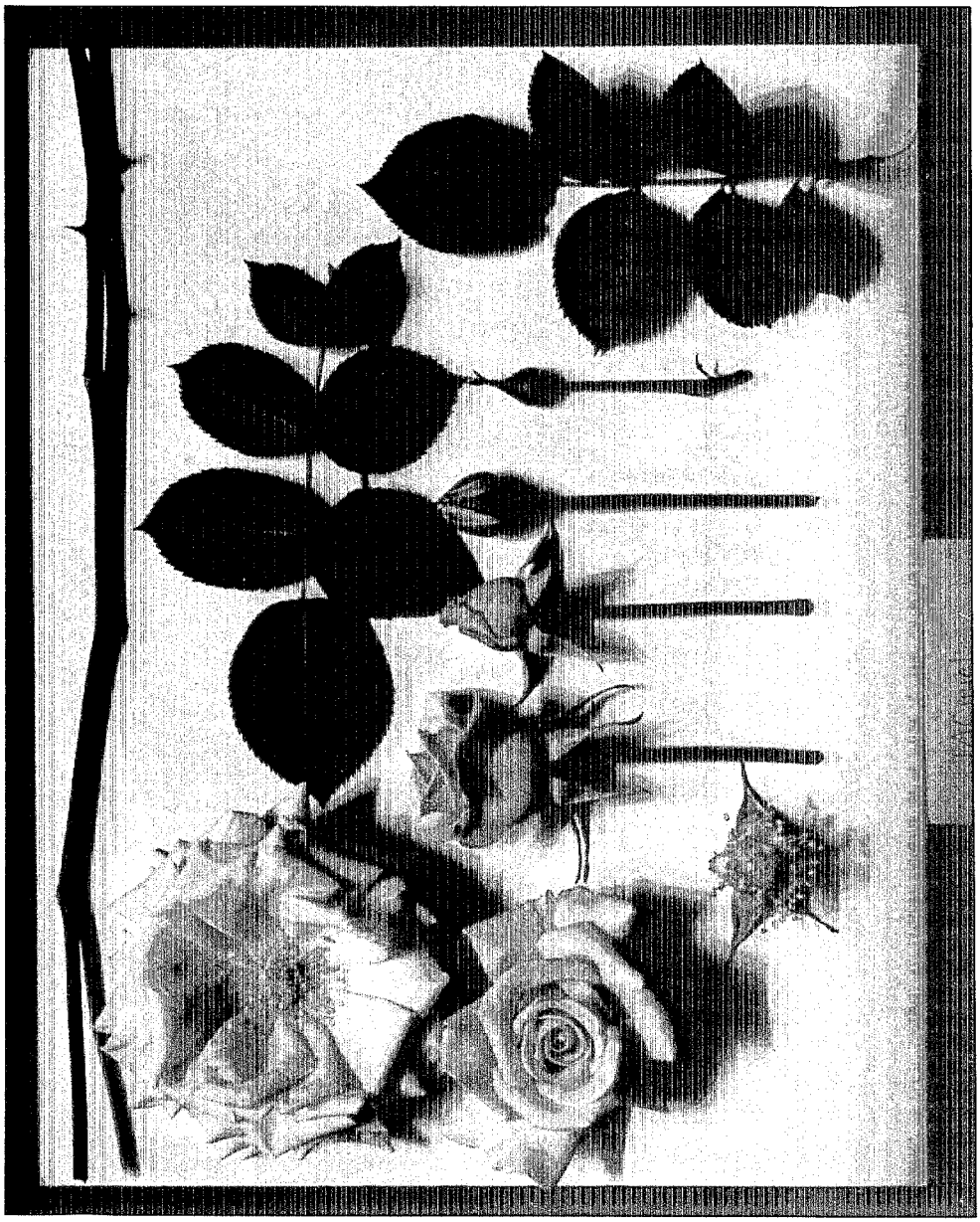

* * * * *